Figure 1:
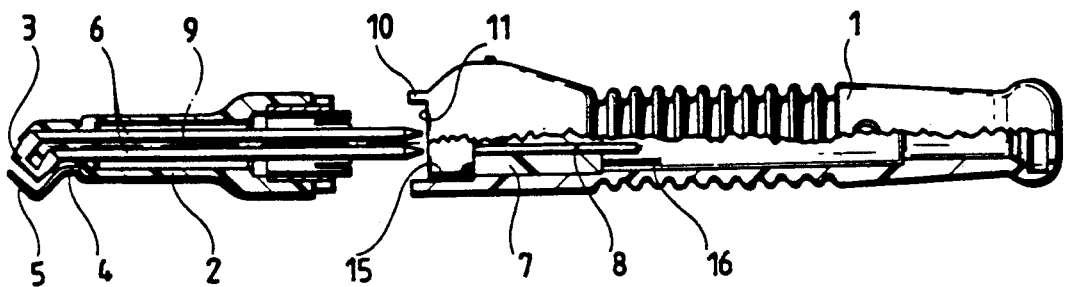

United States Patent [19]

Ettwein et al.

[11] Patent Number: 5,040,975
[45] Date of Patent: Aug. 20, 1991

[54] METHOD AND INSTRUMENT FOR RELEASING A BRACKET

[75] Inventors: Karl-Heiner Ettwein, Remchingen; Friedrich-Wilhelm Röhlcke, Bilfingen; Heinz Bäuerle, Ispringen; Karl-Heinz Reichelt, Keltern; Bernhard Bäzner, Pforzheim, all of Fed. Rep. of Germany

[73] Assignee: Dentaurum J. P. Winkelstroeter KG, Ispringen, Fed. Rep. of Germany

[21] Appl. No.: 521,136

[22] Filed: May 9, 1990

[30] Foreign Application Priority Data

May 13, 1989 [DE] Fed. Rep. of Germany ....... 3915806

[51] Int. Cl.$^5$ .......................... A61C 3/00; A61C 1/00; A61C 19/00
[52] U.S. Cl. .......................................... 433/3; 433/27; 433/32
[58] Field of Search ...................... 433/2, 3, 24, 27, 32

[56] References Cited

U.S. PATENT DOCUMENTS

| 4,155,164 | 5/1979 | White ..................................... 433/3 |
| 4,455,138 | 6/1984 | Sheridan ................................ 433/3 |
| 4,824,366 | 4/1989 | Hohmann et al. .................... 433/32 |
| 4,907,965 | 3/1990 | Martin .................................... 433/3 |

OTHER PUBLICATIONS

John J. Sheridan, D.D.S., M.S.D. et al., "Electrothermal debracketing, Part I, An in vitro study", Am. J. Orthod., Jan. 1986, pp. 21-27, (vol. 89).

John J. Sheridan, D.D.S., M.S.D. et al., "Electrothermal debracketing, Part II, An in vivo study", Am. J. Orthod., 1986, pp. 141-145.

Klaus-Dieter Gerkhardt et al., "Elektrothermische Brackettentfernung durch Erweichung des Klebers mittels Hochstromimpuls"; Prakt. Kieferorthop. 2, pp. 145-148 (1988).

Pamphlet of Scheu-Dental Company published in Oct. 1988.

*Primary Examiner*—John J. Wilson
*Assistant Examiner*—Cindy A. Cherichetti
*Attorney, Agent, or Firm*—Leydig, Voit & Mayer

[57] ABSTRACT

An improved method is proposed for releasing brackets from bonded joints whereby also ceramic brackets can be removed. Herein, the layer of bonding agent is subjected to pulse-shaped heat input by transfer of heat from an instrument to the bracket, with a safety device allowing only a suitable amount of heat for the respective type of bracket to be transferred.

15 Claims, 2 Drawing Sheets

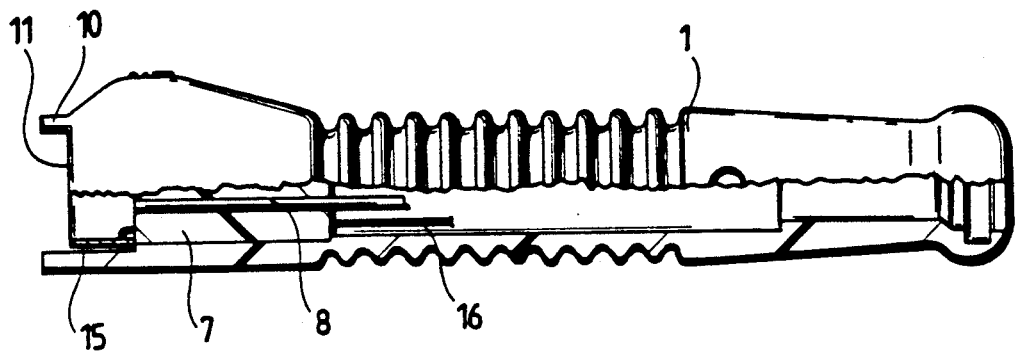
FIG.5
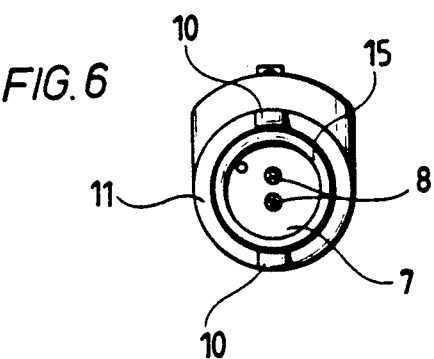
FIG.6
FIG.7
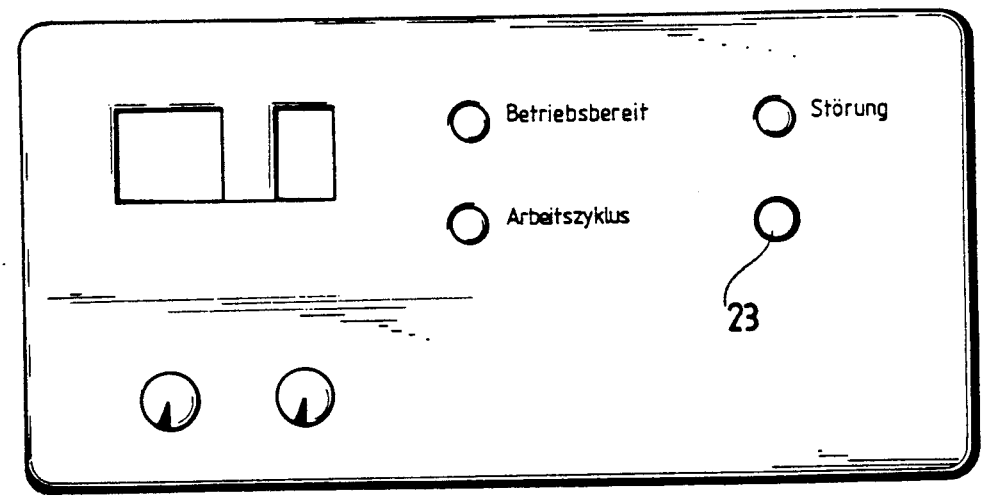

METHOD AND INSTRUMENT FOR RELEASING A BRACKET

The invention relates to a method and an instrument for releasing a bracket from a bonded joint by subjecting the layer of bonding agent located at the base surface of the bracket to pulse-shaped heat input by an instrument.

The removal of metal or ceramic brackets after dentofacial orthopaedic treatment has been and still is predominantly carried out with removing tongs or instruments which are specially shaped for this purpose. When doing so, there is, however, the risk that the bonding agent will remain adhered to the bracket base and that owing to the intimate bond between bonding agent and enamel, tooth enamel prisms will be torn out, which is undesired from a medical point of view. For this reason, during removal of the bracket, separation at the joint boundary between bonding agent and bracket base is desired. A method has recently been marketed for the removal of metal brackets wherein the bonding agent is softened by resistance heating of the metal bracket, thereby enabling simple separation of the bracket from the tooth.

The above-mentioned method is only usable for the removal of metal brackets as their electric conductivity is a precondition of the resistance heating.

When ceramic brackets are removed from teeth with tongs or instruments, there is in addition to the problem of the tooth liaison the disadvantage of bracket breakage owing to the brittleness of the ceramic material. The above-mentioned thermal method, as for metal brackets, is not usable for ceramic brackets because of their electric insulation effect.

The object of the invention is to propose a method for ceramic brackets which excludes the disadvantages mentioned above in connection with ceramic brackets and provides a simple, careful and painless procedure for the doctor and the patient which can be carried out with inconsiderable expenditure of force.

This object was accomplished in accordance with the invention with the method described at the beginning by the heat energy being transferred from a source of heat of the instrument to the bracket, with a safety device of the instrument determining the type of the bracket to be removed prior to or at the beginning of the heat input and permitting during the heat transfer only a quantity of heat which is admissible for the type of bracket.

The most important distinction between the bracket types is governed by their thermal conductivity as the removal of, for example, steel brackets requires a heat pulse of different dimensions than the removal of ceramic brackets.

The bracket type is preferably determined by measurement of the electric conductivity of the bracket material.

It is possible for certain embodiments of the instrument to be designed for exclusive use with ceramic brackets. In the event a metallic bracket material is detected, the safety device then excludes heat transfer by the safety device. The safety device will then preferably generate an alarm signal which calls the operator's attention to this fact.

In particularly preferred methods, the amount of heat to be transferred is predetermined, in particular in dependence upon the bracket to be detached, with the size of the bracket and its structure at the base surface which may contain larger or smaller amounts of the bonding agent being taken into consideration. To prevent overheating of the source of heat and/or the brackets or the patient's teeth, it is expedient for the pulse-shaped heat input to be permitted only after a minimum time interval.

An instrument suitable for performance of the inventive method includes a head piece and a handle part, with the handle part comprising a source of heat which can be brought into contact with the bracket and a safety device for metering the heat input.

The safety device is preferably equipped with a sensor which delivers a control signal in dependence upon the electric conductivity of the bracket material.

In dependence upon this sensor signal, either the bracket can be subjected to an adapted heat input via the source of heat or as, for example, with instruments equipped only for use with ceramic brackets, heat input to the brackets can be totally excluded in the case of metallic brackets.

The source of heat itself is preferably in the form of an electric heating element. Holding elements for the detached bracket are preferably arranged adjacent to the source of heat so the bracket is held on the instrument after detachment.

In a particularly preferred embodiment, the holding element may be an auxiliary electrode of the sensor, and the electric heating element itself may be used as second auxiliary electrode. The sensor signal is then determined by the current flowing between holding element and heat element.

The heating element is preferably of bow-shaped design so as to be insertable into a gap of the bracket. Hence if the heating element is of corresponding stability, a shearing motion can be exerted on the bracket with the instrument and the detachment of the bracket from the bonded joint thereby accelerated.

It is preferable for the heating element to be of such design that the current leads have a distinctly lower temperature than the actual heating segment. Aside from an enlargement of the cross-section, this is also achievable by a special surface design which enables good radiation of heat energy. This ensures that the heat energy is mainly transferred to the bracket by the heating segment and not by further parts of the heating element, which results in a very precisely defined temperature profile in the bracket itself. For detachment of the bracket from the tooth in as rapid and careful a manner as possible, the base surface of the bracket which represents the transition to the layer of bonding agent should be heated as uniformly as possible.

The division of the instrument into a head piece and a handle part, with the head piece being of removable design, enables exchange of the head piece and hence, for example, adaptation to various bracket shapes or also disinfection of the head piece which is the only part to come into contact with the patient's mouth.

If the heating element is to be used in addition for transferring mechanical forces to the bracket, it is recommendable to provide a means for preventing rotation between head piece and handle part.

Figure 2:
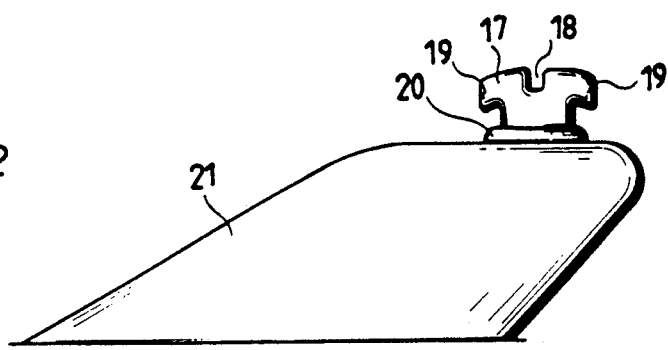
Figure 3:
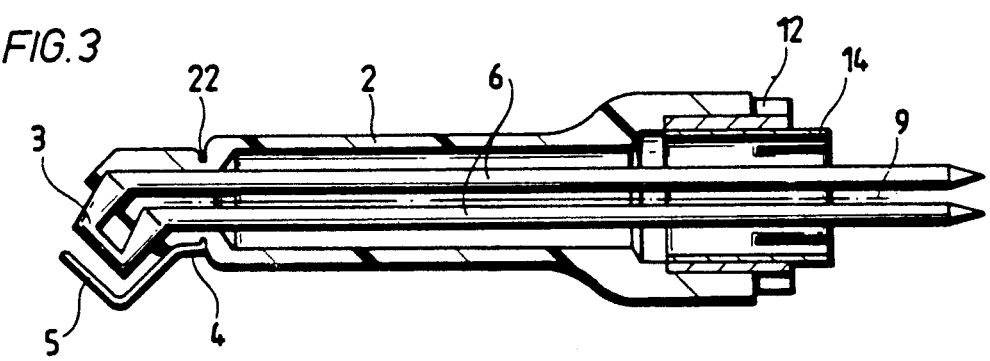
Figure 4:
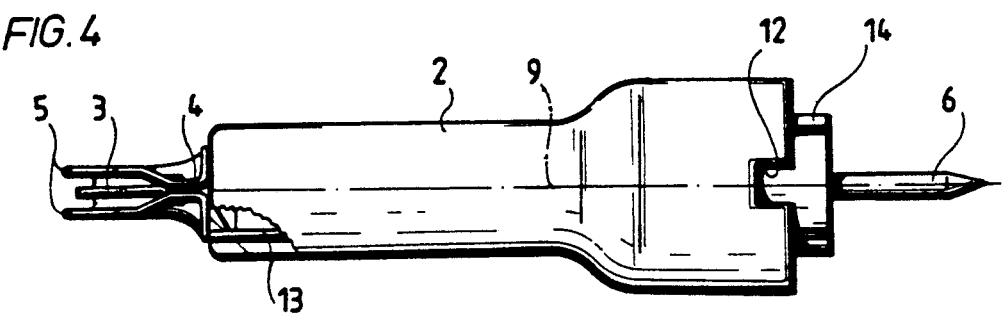

Further advantageous configurations are apparent from the description with reference to the appended drawings which show in detail:

FIG. 1 an inventive instrument with handle part and head piece separated from each other;

FIG. 2 a bracket bonded to a schematically illustrated tooth;

FIG. 3 a sectional view of a head piece of an inventive instrument;

FIG. 4 a side view of the head piece of FIG. 3;

FIG. 5 a partly broken-open illustration of the handle part;

FIG. 6 a plan view of the handle part of FIG. 5; and

FIG. 7 a schematically illustrated supply unit for the instrument according to the invention.

In operation of the instrument for releasing ceramic brackets, the bracket is heated for a short time by means of heat transfer in order to soften the bonding agent. The heat transfer is achieved by resistance heating of an electrode (3) which is introduced into the slot (18) of the ceramic bracket (17). A current pulse of short duration is directed through the electrode (3) consisting of heat-resistant material via the conductors (6). Owing to the ohmic resistance of the electrode (3), the current pulse results in intensive heating of the latter, which is transferred to the ceramic bracket. As the heating is carried out via the bracket, a weakening of the adherence of the bonding agent at the boundary layer between bracket and bonding agent is achieved. Hence the breaking point also occurs here. To prevent harmful heating of the tooth, the total energy can be metered via the pulse duration. A slight torsional movement of the bracket following the heat pulse results in removal of the bracket. The metering of the energy may be varied by a control means. It is also conceivable for a change in the duration of the pulse to be brought about via a rotary switch (23) on the front panel of the instrument.

To avoid overheating of the electrode, the instrument is programmed for the next pulse to be triggered only after a certain time.

For ergonomic reasons, the electrode (3) is inclined at a certain angle to the center axis (9). In this way, the brackets, above all on the back molars, can be reached without difficulty.

The holding spring (4) is of such design that when the electrode (3) is inserted, the legs (5) of the holding spring (4) snap over the wings (19) of the ceramic bracket (17). Hence when the bracket is released, the holding spring (4) prevents it from falling into the patient's mouth as it presses the bracket (17) against the electrode (3). To enable all kinds of ceramic brackets to be held, holding springs of different shapes may be used. It is, therefore, necessary for the holding springs to be exchangeable in a problem-free manner. This was achieved by the holding springs being pushed onto the tip of the head piece (2) only. When doing so, care must be taken to ensure that the ring of the holding springs snaps into the ring groove (22). By slightly spreading the spring, the latter can be removed from the head piece (2) and replaced by another one.

The head piece (2) can be separated from the handle (1) by simple withdrawal. This advantage and the use of a suitable material enable sterilisation of the head piece (2) which comes into contact with the patient.

The two noses (10) on the end face (11) of the handle (1) enter the groove (12) of the head piece (2) when the two parts are put together, thereby preventing the head piece (2) from turning and ensuring that it is precisely seated. The head piece (2) may be positioned on the handle (1) in any desired manner but the noses (10) must go into the groove (12). When the head piece (2) and the handle (1) are joined, the conductors (6) are pushed into the sockets (7) of the handle (1). The sockets are connected to the instrument via the cable (8).

The current pulse can be triggered via a foot switch. It is, however, also conceivable for the pulse to be triggered by a small push-button switch mounted in the handle (1).

The readiness for operation is indicated by an optical signal given by an LED on the front panel of the instrument and on the handle (1). The duration of the debonding cycle is likewise indicated by an optical signal on the front panel of the instrument and on the handle (1). It is not possible for a current pulse to be triggered if the instrument is malfunctioning. In addition, malfunction is made visible by an optical flashing signal on the front panel of the instrument.

Metal brackets cannot be removed with the instrument designed for detaching ceramic brackets. They are heated, but the heat energy is insufficient to soften the bonding agent (20) at the transition between metal and bonding agent. Hence there is the danger that the temperature of the tooth will increase to such an extent that the tooth will be damaged or even destroyed. For this reason, the holding spring (4) is used as sensor which recognizes whether the electrode (3) is pushed onto a ceramic or metal bracket. In the ring groove (22), the ring of the holding spring (4) makes contact with the wire (13) which is soldered to the clamping sleeve (14). When the head piece (2) is placed on the handle (1), the clamping sleeve (14) makes contact with the sleeve (15). The sleeve (15) is connected to the electronic system of the instrument via the signal cable (16). When the electrode (3) is pushed onto a metal bracket, a current-conducting connection is established between the holding spring (4) and the electrode (3). This contact causes an acoustic signal to be triggered by an electronic circuit. The electronic system is programmed so that triggering of a current pulse is not possible as long as the contact exists between holding spring and electrode.

The present disclosure relates to the subject matter disclosed in German application No. P 39 15 806.3-35 of May 13, 1989, the entire specification of which is incorporated herein by reference.

We claim:

1. A method for releasing a bracket from a bonded joint by softening a layer of bonding agent located at the base surface of said bracket comprising:
   contacting said bracket with a means for generating heat through the application of energy thereto;
   determining an electrical characteristic of the bracket; and
   selectively applying energy to the means for generating heat depending upon said electrical characteristic of the bracket.

2. The method according to claim 1 wherein the electrical characteristic determined is the electrical conductivity of the bracket material.

3. The method according to claim 2 wherein energy is not applied to the means for generating heat if the bracket material is determined to be electrically conductive.

4. The method of claim 1 wherein the amount of energy to be applied to said means for generating heat is contained in a predetermined pulse.

5. The method of claim 4 wherein further energy may be applied to said means for generating heat only after a minimum time interval.

6. Instrument for removing a bracket from a bonded joint by heating a layer of bonding agent located on the base surface of said bracket, said instrument comprising handle means and
head means, said head means comprising means for generating heat with the passage of electricity therethrough which can be brought into contact with said bracket, and safety means for sensing an electrical characteristic of the bracket and preventing the application of electricity to the means for generating heat if said electrical characteristic is present.

7. Instrument according to claim 6 wherein the safety means comprises means for sensing the electrical conductivity of the bracket material.

8. Instrument according to claim 6 wherein means for holding the bracket are arranged adjacent the means for generating heat.

9. Instrument according to claim 6 wherein the means for generating heat is designed as a bow which is insertable into a slot in said bracket.

10. Instrument according to claim 6 wherein said head means further comprise a sleeve through which insulated leads pass for supplying energy to the means for generating heat.

11. Instrument according to claim 6 wherein the head means are removable from the handle means.

12. Instrument according to claim 6 wherein the head means can be sterilized.

13. Instrument according to claim 8 wherein the means for holding the bracket serve as electrode means for sensing an electrical characteristic of the bracket material.

14. Instrument according to claim 13 wherein the means for generating heat serve as electrode means for sensing an electrical characteristic of the bracket material.

15. Instrument according to claim 11 wherein the head means can be sterilized.

* * * * *

UNITED STATES PATENT AND TRADEMARK OFFICE
CERTIFICATE OF CORRECTION

PATENT NO. : 5,040,975
DATED : August 20, 1991
INVENTOR(S) : Karl-Heiner Ettwein, et al.

It is certified that error appears in the above-identified patent and that said Letters Patent is hereby corrected as shown below:

In FIG. 7 of the Drawings:

Delete "Betriebsbereit" and substitute --READY--

Delete "Arbeitszyklus" and substitute --DEBONDING CYCLE--

Delete "Storung" and substitute --SERVICE--

Signed and Sealed this

Twenty-sixth Day of January, 1993

*Attest:*

STEPHEN G. KUNIN

*Attesting Officer*  Acting Commissioner of Patents and Trademarks